United States Patent
Khalaj

(10) Patent No.: US 10,159,817 B2
(45) Date of Patent: Dec. 25, 2018

(54) OVER-THE-NEEDLE CATHETER SLEEVE

(71) Applicant: Avent, Inc., Alpharetta, GA (US)

(72) Inventor: Steve Saeed Khalaj, Laguna Hills, CA (US)

(73) Assignee: Avent, Inc., Alpharetta, GA (US)

( * ) Notice: Subject to any disclaimer, the term of this patent is extended or adjusted under 35 U.S.C. 154(b) by 897 days.

(21) Appl. No.: 14/306,551

(22) Filed: Jun. 17, 2014

(65) Prior Publication Data

US 2015/0360003 A1  Dec. 17, 2015

(51) Int. Cl.
| | | |
|---|---|---|
| A61M 31/00 | (2006.01) | |
| A61M 37/00 | (2006.01) | |
| A61M 25/06 | (2006.01) | |
| A61M 25/00 | (2006.01) | |

(52) U.S. Cl.
CPC .. *A61M 25/0606* (2013.01); *A61M 2025/0059* (2013.01); *A61M 2025/0681* (2013.01)

(58) Field of Classification Search
CPC .. A61M 2025/0059; A61M 2025/0681; A61M 25/0606
USPC .......................................................... 604/510
See application file for complete search history.

(56) References Cited

U.S. PATENT DOCUMENTS

| | | |
|---|---|---|
| 4,828,549 A | 5/1989 | Kvalo |
| 4,985,022 A | 1/1991 | Fearnot et al. |
| 8,303,570 B2 | 11/2012 | Gregorich et al. |
| 8,611,993 B2 | 12/2013 | Vitullo et al. |
| 2005/0090801 A1* | 4/2005 | Racz .................. A61M 25/0097 604/500 |
| 2006/0135973 A1* | 6/2006 | Hawkins ............ A61B 17/3415 606/167 |
| 2009/0187140 A1 | 7/2009 | Racz |
| 2010/0160863 A1 | 6/2010 | Heuser |

FOREIGN PATENT DOCUMENTS

WO  WO 2014/074237 A1  5/2014

OTHER PUBLICATIONS

International Search Report and Written Opinion for PCT/US2015/035039, dated Nov. 17, 2015, 17 pages.

* cited by examiner

*Primary Examiner* — Jason Flick
(74) *Attorney, Agent, or Firm* — Dority & Manning, P.A.

(57) ABSTRACT

The present disclosure is directed to an over-the-needle (OTN) catheter assembly having a sleeve configured thereon. The catheter includes a body having an outer diameter. The body also includes a proximal end and a distal end and defines a lumen extending from the proximal end to the distal end. A needle is configured within the lumen of the catheter and extends from the proximal end to the distal end. The sleeve is configured around a portion of the outer diameter of the catheter that passes through an insertion site of the catheter. Further, the sleeve includes a length extending from a first end to a second end and is configured to prevent the catheter from collapsing along the length of the sleeve. In addition, the sleeve is configured to prevent leakage from the insertion site of the catheter.

8 Claims, 4 Drawing Sheets

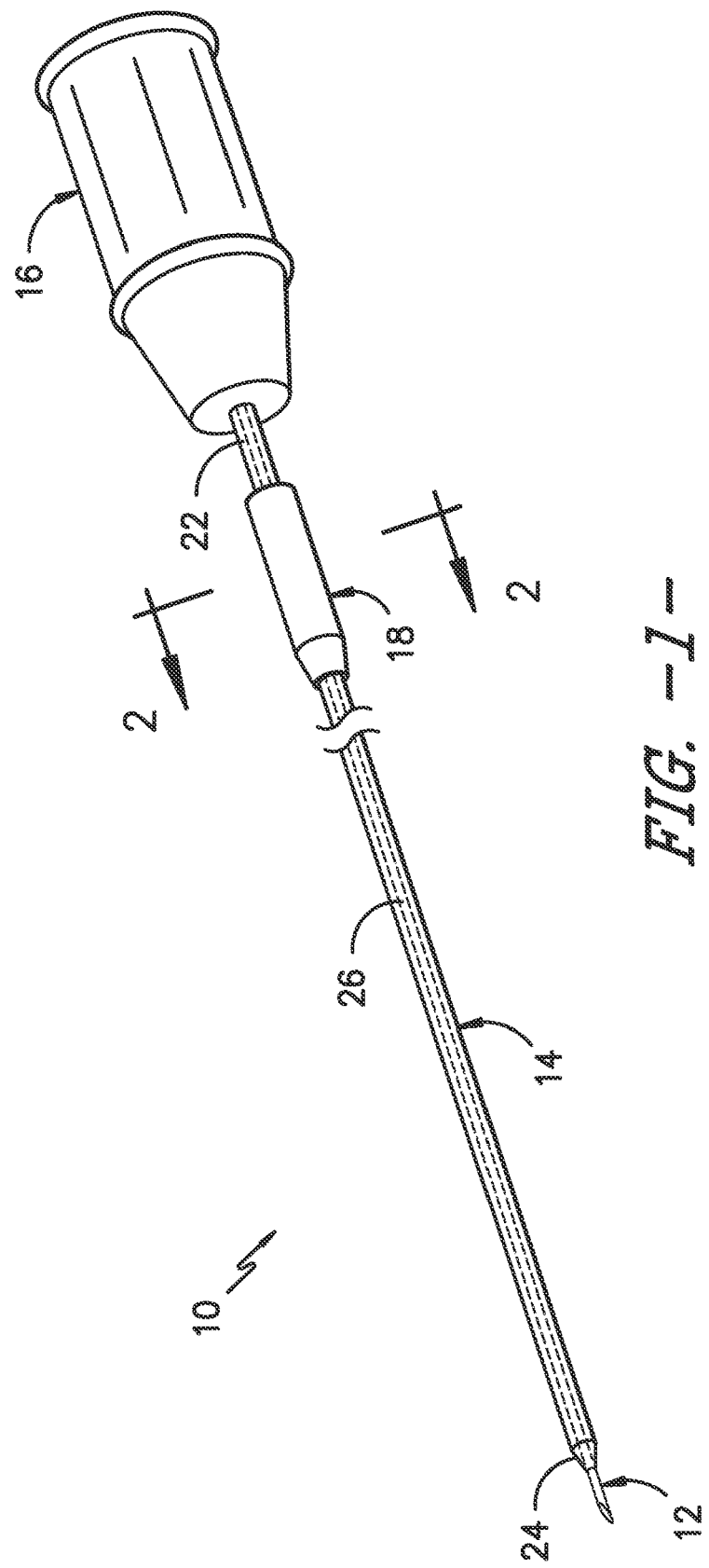
FIG. -1-

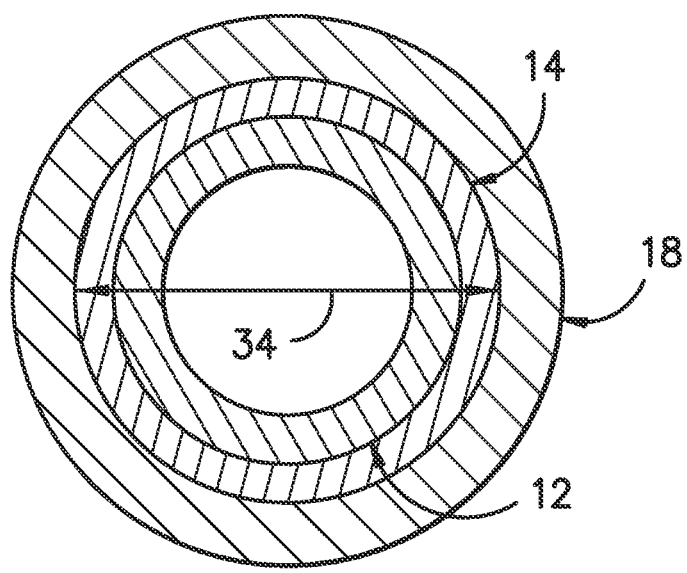
FIG. -2-
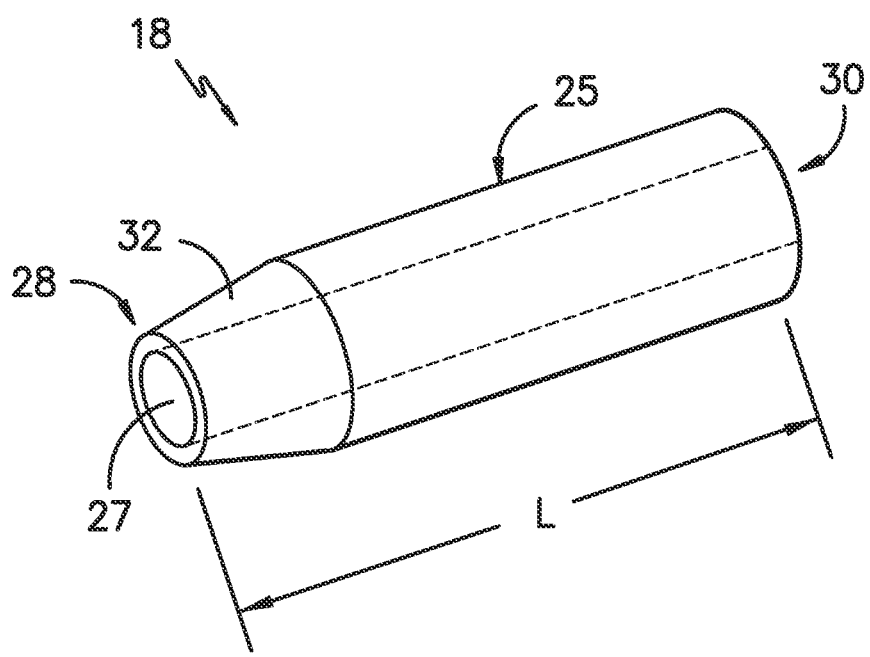
FIG. -3-

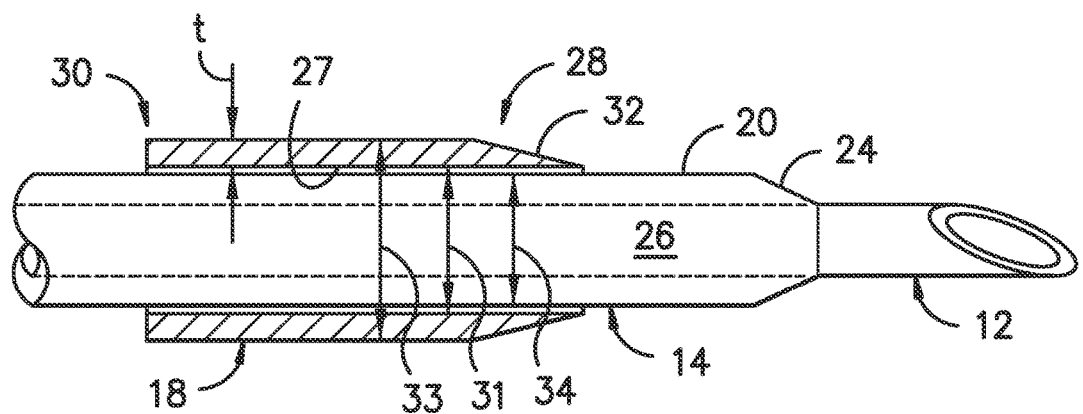
FIG. -4-
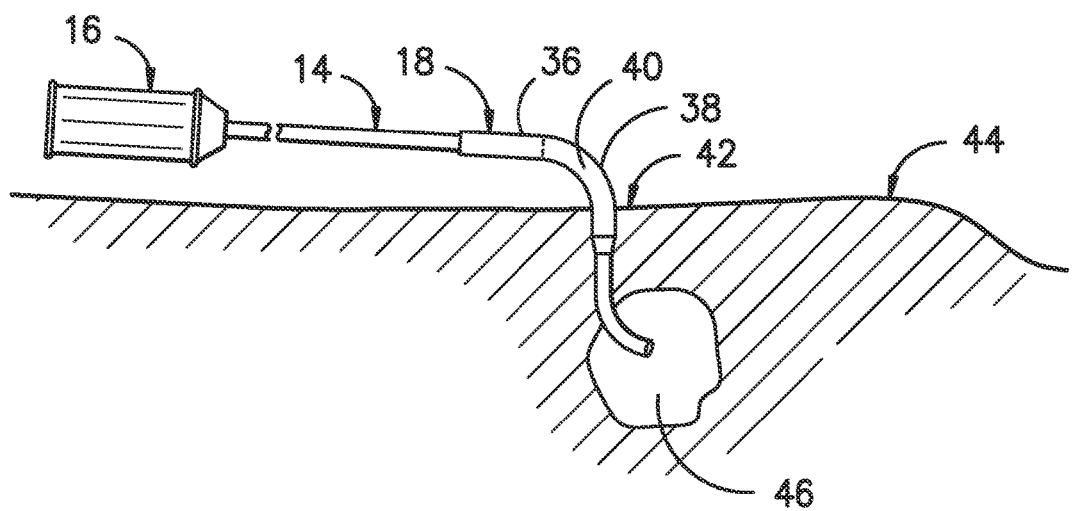
FIG. -5-

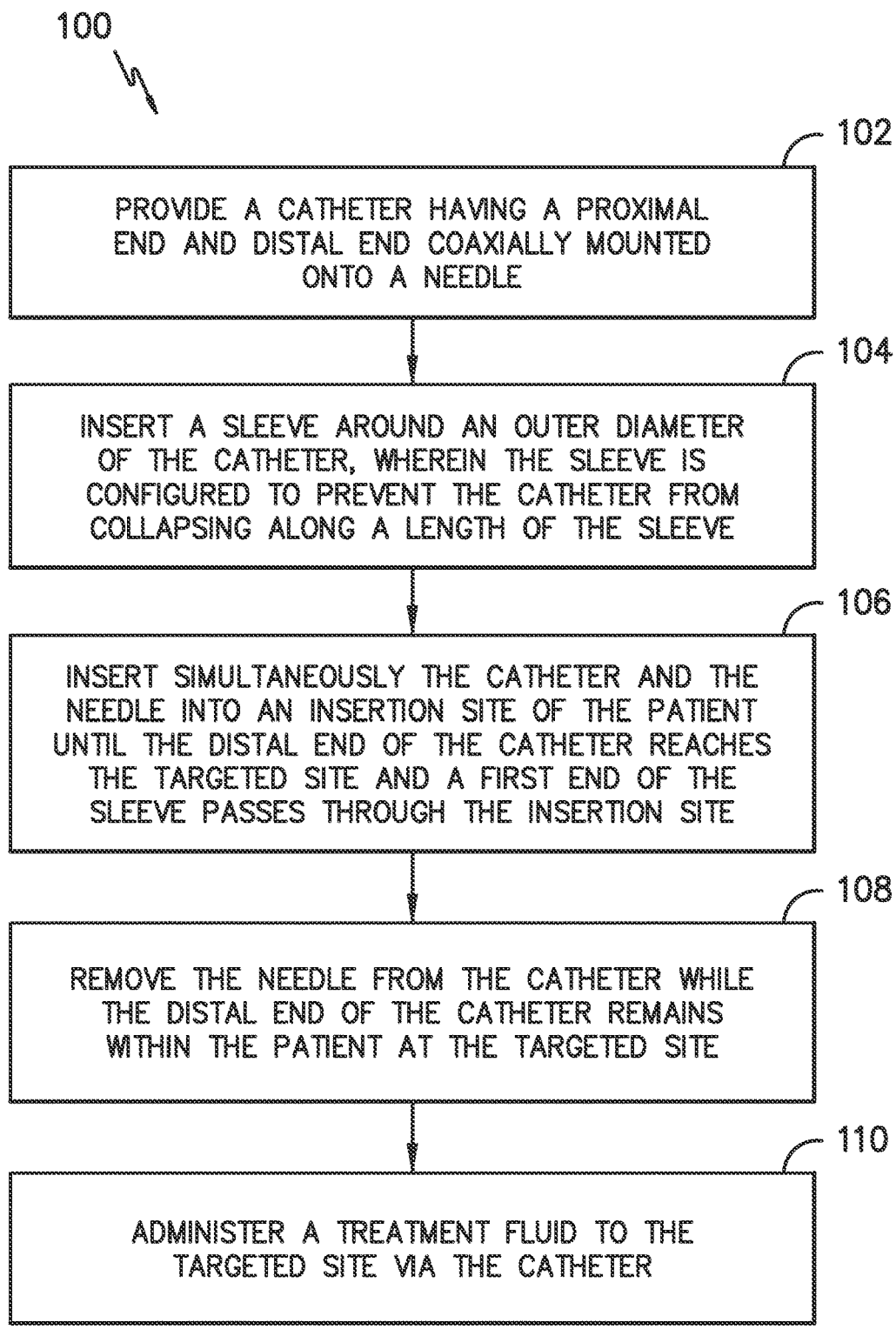
FIG. -6-

OVER-THE-NEEDLE CATHETER SLEEVE

FIELD OF THE INVENTION

The present invention relates generally to the field of medical catheters and more particularly to over-the-needle (OTN) catheters.

BACKGROUND

Devices used to administer a fluid inside the anatomy of a patient are well known. For example, hypodermic needles, catheters, and the like are often used to deliver medication and other fluids to targeted sites within the body. In many instances, catheters are preferred because they can deliver fluid to a particular site over a period of time. Since catheters are generally made of a flexible plastic material, a needle is typically used to insert the catheter within a patient. For example, certain catheters, generally referred to as "through-the-needle" catheters, often require stiff, hollow introducer needles for placement within the anatomy. Thus, the catheter can be inserted through the needle after the needle is located at the targeted site. Typically, such introducer needles have sharp tips that may damage tissue and/or nerves during their delivery into a body, thus causing discomfort for the patient.

Another type of catheters, generally referred to as "over-the-needle" (OTN) catheters, include a catheter coaxially mounted onto a needle. In this type of catheter, the catheter and the needle may be inserted into a patient together. Once the catheter and the needle are located at the targeted site, the needle can be removed, leaving the catheter in place. Thus, OTN catheters can be purposely directed to an exact location without the need to thread the catheter within a patient. Accordingly, OTN catheters have gained increased attention in regard to delivering anesthetic medication, for example, for the purposes of nerve block.

It is desired to design OTN catheters with thin walls so as to decrease discomfort to the patient and to minimize leakage at the insertion site of the catheter. Such thin walls, however, can increase the catheter's susceptibility to kinking or collapsing when being inserted within a patient.

Accordingly, the present invention is directed to a sleeve for an OTN catheter that addresses the aforementioned problems.

SUMMARY OF THE INVENTION

Objects and advantages of the invention will be set forth in part in the following description, or may be obvious from the description, or may be learned through practice of the invention.

In certain aspects, the present invention relates to an over-the-needle (OTN) catheter assembly having a sleeve configured thereon. The catheter includes a body having an outer diameter. The body also includes a proximal end and a distal end and defines a lumen extending from the proximal end to the distal end. A needle is configured within the lumen of the catheter and extends from the proximal end to the distal end. The sleeve is configured around the portion of the outer diameter of the catheter that passes through an insertion site of a patient. Further, the sleeve has a length extending from a first end to a second end that is configured to prevent the catheter from collapsing along the length of the sleeve. The sleeve is also configured to minimize leakage from the insertion site of the catheter.

In one embodiment, the first end of the sleeve includes a tapered edge. Thus, the tapered edge is configured to minimize discomfort of the patient at the insertion site of the catheter. In another embodiment, the sleeve may include a substantially linear portion and a substantially angled portion. More specifically, the angled portion may include at least one bend configured to prevent leakage from the insertion site of the catheter, e.g. blood, medications, or similar. In certain embodiments, the bend may include a substantially 90-degree angle. In further embodiments, the bend may include any other suitable angle as well.

In additional embodiments, the length of the sleeve may range from about 0.5 inches to about two inches, e.g. about one inch. In still further embodiments, the length of the sleeve may be less than 0.5 inches or more than two inches. In another embodiment, the sleeve may be constructed of a flexible material. For example, in various embodiments, the flexible material may include at least one of or a combination of the following: a rubber material, a silicone material, a polymeric material, an elastomeric material, or similar.

In another aspect, the present invention relates to a sleeve for an over-the-needle (OTN) catheter. The sleeve includes a body having a length extending from a first end to a second end. The body includes a hollow passageway extending from the first end to the second end. The hollow passageway is configured to fit around a portion of an outer diameter of the catheter. More specifically, the hollow passageway is configured to fit around the portion of the outer diameter of the catheter that passes through an insertion site of a patient. The body further includes a linear portion and an angled portion. Thus, the body is configured to prevent the catheter from collapsing along the length of the sleeve and the angled portion is configured to prevent leakage from the insertion site of the patient. It should be understood that the sleeve may also be configured with any of the additional features as described herein.

In yet another aspect, the present invention relates to a method for using an over-the-needle catheter assembly to provide treatment to a targeted site within a patient. The method includes a step of providing a catheter having a proximal end and distal end, the catheter coaxially mounted onto a needle. Another step includes inserting a sleeve around an outer diameter of the catheter, wherein the sleeve is configured to prevent the catheter from collapsing along a length of the sleeve. Still another step includes inserting simultaneously the catheter and the needle into an insertion site of the patient until the distal end of the catheter reaches the targeted site and a first end of the sleeve passes through the insertion site. The method also includes removing the needle from the catheter while the distal end of the catheter remains within the patient at the targeted site. Another step includes administering a treatment fluid to the targeted site via the catheter. It should be understood that the method may also include any of the additional steps and/or features as described herein.

For example, in one embodiment, the method may further include bending the sleeve such that the sleeve has a linear portion and an angled portion. Thus, in another embodiment, after inserting simultaneously the catheter and the needle into the insertion site of the patient, the angled portion may pass through the insertion site of the catheter so as to prevent leakage from the insertion site and the linear portion may remain outside of the patient.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a perspective view of one embodiment of an OTN catheter assembly in accordance with aspects of the invention;

FIG. 2 illustrates a cross-sectional view of one embodiment of an OTN catheter assembly in accordance with aspects of the invention;

FIG. 3 illustrates a perspective view of a sleeve for an OTN catheter assembly in accordance with aspects of the invention;

FIG. 4 illustrates a side, cross-sectional view of one embodiment of an OTN catheter assembly in accordance with aspects of the invention;

FIG. 5 illustrates a perspective view of one embodiment of an OTN catheter assembly inserted into a patient in accordance with aspects of the invention; and FIG. 6 illustrates a flow diagram of one embodiment of a method for using an OTN catheter assembly to provide treatment to a targeted site within a patient in accordance with aspects of the invention.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The positional terms "proximal" and "distal" are used herein to orient the various components relative to each other and to the patient. "Distal" refers to the direction that is closest to the wound site (e.g., the distal end of the catheter is the end oriented towards a catheter insertion site), and "proximal" refers to the opposite direction (e.g., the proximal end of the catheter is typically inserted into a catheter connector, which in turn is typically connected to a fluid delivery device).

Generally, the present disclosure is directed to a sleeve for an over-the-needle (OTN) catheter assembly that prevents the catheter from collapsing along a length of the sleeve and minimizes leakage at an insertion site of the catheter. The OTN catheter assembly includes a catheter coaxially mounted onto a needle. The catheter includes a body having an outer diameter. The body of the catheter has a proximal end and a distal end and defines a lumen extending from the proximal end to the distal end. The sleeve is configured around the portion of the outer diameter of the catheter that passes through the insertion site. Thus, the sleeve provides extra tubing that adds strength to the catheter so as to prevent the catheter from collapsing along a length thereof. Further, the sleeve typically includes a bend that minimizes leakage at the insertion site of the catheter.

Referring now to the drawings, various embodiments of an over-the-needle (OTN) catheter assembly 10 according to the present disclosure are illustrated. For example, as shown in FIG. 1, the catheter assembly 10 includes a catheter 14 having a body 20 with a proximal end 22 and distal end 24 coaxially mounted onto a needle 12. In certain embodiments, the proximal end 22 may include a hub 16 configured thereon for mating communication with a fluid delivery device (not shown). As mentioned, the fluid delivery device may be any suitable device known in the art, such as a pump, reservoir, syringe, or the like. Further, the hub 16 may have any conventional configuration, such as a Luer-lock fitting.

The body 20 of the catheter 14 defines a lumen 26 extending from the proximal end 22 of the catheter 14 to the distal end 24. Further, as shown in FIG. 2, the catheter 14 has an outer diameter 34 defined by an outer surface of the catheter wall. In accordance with aspects of the present disclosure, a sleeve 18 is configured around at least a portion of the outer diameter 34 of the catheter 14. More specifically, as shown in FIG. 3, the sleeve 18 includes a body 25 having a length L extending from a first end 28 to a second end 30. It should be understood that the length L of the sleeve 18 may be any suitable length so as to cover any suitable length of the catheter 14. For example, in certain embodiments, the length L of the sleeve 18 ranges from about 0.5 inches to about two inches, preferably about 1 inch. In additional embodiments, the length L of the sleeve 18 may be less than 0.5 inches or more than two inches.

Referring particularly to FIG. 2, the body 25 of the sleeve 18 defines a hollow passageway 27 extending from the first end 28 to the second end 30. As shown, the hollow passageway 27 is sized so as to receive the outer diameter 34 of the catheter 14. For example, as shown in FIG. 4, the hollow passageway 27 may have an inner diameter 31 that is slightly larger than the outer diameter 34 of the catheter 14 such that the sleeve 18 can be easily slid over the catheter 14.

It should be understood that the sleeve 18 as described herein may be constructed of any suitable, flexible material. For example, in certain embodiments, the sleeve 18 may be formed of a material that is rigid enough to keep its shape, yet flexible enough to curve with the shape of the catheter 14. More specifically, the sleeve 18 may constructed of a flexible material, such as plastic, rubber, a polymeric material, silicone, an elastomeric material, or any other suitable material. Further, in certain embodiments, the sleeve 18 may be constructed of polyisoprene, polyurethane, styrene butadiene, and/or any other suitable flexible material. As such, the sleeve 18 may be bendable, as is discussed in more detail below. In addition, the material of the sleeve 18 may be designed such that the sleeve 18 easily slides along the catheter 14 for example, by choosing materials that provide a low the coefficient of friction therebetween.

Referring now to FIGS. 1 and 4-5, the sleeve 18 may be included as part of the OTN assembly 10 to prevent the catheter 14 from collapsing along a length of the sleeve 18 and to prevent leakage at the insertion site 42 of the catheter 14. Initially, the sleeve 18 may be included near the hub 16 of the catheter 14. Thus, the sleeve 18 is configured to slide along the outer diameter 34 of the catheter 14 by a user such that the user can place the sleeve 18 at any suitable location along the length of the catheter 14. For example, as shown in FIGS. 4 and 5, the sleeve 18 is located closer to the distal end 24 of the catheter 14 than the proximal end 22 of the catheter 14. Thus, as the distal end 24 of the catheter 14 is inserted into the patient, a user can move the sleeve along the outer diameter 34 of the catheter 14 such that it is located at the insertion site 42 of the catheter 14. In alternative embodiments, the sleeve 18 may be located closer to the proximal end 22 of the catheter 14 than the distal end 24 of the catheter 14.

Referring to FIG. 5, the first end 28 of the sleeve 18 may be configured to be easily inserted into the patient 44 at the insertion site 42. More specifically, in certain embodiments, the sleeve 18 may include a tapered edge 32 to assist with inserting the sleeve 18 into a patient 44. For example, as shown in FIG. 4, the inner and outer diameters 31, 33 of the sleeve 18 generally define a thickness t therebetween. Thus, the tapered edge 32 generally tapers from the outer diameter 33 to the inner diameter 31 such that the thinnest portion of the tapered edge 32 is slightly larger than the outer diameter 34 of the catheter 14. Accordingly, the tapered edge 32 may be easily inserted into the insertion site 42 of the patient 44 along with the catheter 14 without increasing discomfort to the patient.

In addition, as mentioned, the sleeve 18 can be constructed of a flexible and/or bendable material such that a user can bend the sleeve 18 to create a linear portion 36 and an angled portion 38 as shown in FIG. 5. More specifically, the angled portion 38 may include a bend 40 having a substantially 90-degree angle other than 90 degrees. In further embodiments, the bend 40 may have any suitable angle. For example, the bend 40 may have an angle less than 90 degrees or an angle greater than 90 degrees. Thus, a user can locate the sleeve 18 in the desired location along the length of the catheter 14 and then bend the sleeve 18 to the desired angle. In one embodiment, for example, as user can slide the sleeve 18 to a location near the insertion site 42 of the catheter 14, bend the sleeve 18 to the desired angle, and then insert the first end 28 of the sleeve 18 into the patient 44 such that the bend 40 is located at the insertion site 42. Thus, the sleeve 18 (particularly the bend 40) helps to minimize leakage, e.g. blood, medications, etc., from the insertion site 42.

Referring now to FIG. 6, a flow diagram of one embodiment of a method 100 for using an over-the-needle catheter assembly to provide treatment to a targeted site within a patient is illustrated. As shown in the illustrated embodiment, the method 100 includes a step 102 of providing a catheter having a proximal end and distal end coaxially mounted onto a needle. Another step 104 includes inserting a sleeve around an outer diameter of the catheter. As mentioned, the sleeve is configured to prevent the catheter from collapsing along a length of the sleeve. In additional embodiments, the method 100 may also include bending the sleeve such that the sleeve has a linear portion and an angled portion. The method 100 also includes inserting simultaneously the catheter and the needle into an insertion site of the patient until the distal end of the catheter reaches the targeted site and a first end of the sleeve passes through the insertion site (step 106). More specifically, in certain embodiments, the angled portion of the sleeve may be located at the insertion site, such that a bend in the angled portion minimizes leakage from the insertion site. Once the catheter has been inserted and the sleeve properly placed, the method 100 may also include removing the needle from the catheter while the distal end of the catheter remains within the patient adjacent to the targeted site (step 108). A next step 110 includes administering a treatment fluid to the targeted site via the catheter. As mentioned, the sleeve provides strength to the catheter along the length of the sleeve and includes a bend at the insertion site that minimizes leakage therefrom.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. An over-the-needle catheter assembly, comprising:
   a catheter comprising a body having an outer diameter, said body comprising a proximal end and a distal end, said body defining a lumen extending from said proximal end to said distal end;
   a hub secured at the proximal end of the catheter;
   a needle configured within the lumen of the catheter, said needle extending from said proximal end to said distal end; and,
   a sleeve secured around a distal portion of said outer diameter of said catheter, said sleeve spaced apart and away from the hub such that the sleeve does not contact the hub and passes through an insertion site of a patient, said sleeve comprising a length extending from a first end to a second end, wherein said sleeve is configured to prevent said catheter from collapsing along said length of said sleeve.

2. The catheter assembly of claim 1, wherein said first end of said sleeve comprises a tapered edge, said tapered edge configured to be inserted into the insertion site of the patient.

3. The catheter assembly of claim 1, wherein said sleeve further comprises a substantially linear portion and a substantially angled portion.

4. The catheter assembly of claim 3, wherein said angled portion comprises at least one bend configured to prevent leakage from the insertion site of the patient.

5. The catheter assembly of claim 4, wherein said bend comprises a substantially 90-degree angle.

6. The catheter assembly of claim 1, wherein said length of said sleeve ranges from about 0.5 inches to about two inches.

7. The catheter assembly of claim 1, wherein said sleeve further comprises a flexible material.

8. The catheter assembly of claim 7, wherein said flexible material further comprises at least one of or a combination of the following: a rubber material, a silicone material, a polymeric material, or an elastomeric material.

\* \* \* \* \*